US006372760B1

(12) United States Patent
Kato et al.

(10) Patent No.: US 6,372,760 B1
(45) Date of Patent: Apr. 16, 2002

(54) STABILIZED COMPOSITION COMPRISING ANTIDEMENTIA MEDICAMENT

(75) Inventors: Akira Kato, Ibaraki; Tsutomu Harada; Naokazu Murahashi, both of Aichi; Yukiko Sugaya, Ibaraki; Hidenobu Ando, Gunma, all of (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/700,342

(22) PCT Filed: Mar. 31, 1999

(86) PCT No.: PCT/JP99/01686

§ 371 Date: Jan. 4, 2001

§ 102(e) Date: Jan. 4, 2001

(87) PCT Pub. No.: WO00/59544

PCT Pub. Date: Oct. 12, 2000

(51) Int. Cl.⁷ .............................................. A61K 31/445
(52) U.S. Cl. ........................ 514/319; 514/316; 514/321
(58) Field of Search ................................. 514/319, 316, 514/321

(56) References Cited

U.S. PATENT DOCUMENTS

| 4,567,202 A | * | 1/1986 | Diir et al. | 514/656 |
| 5,428,043 A | * | 6/1995 | Chen | 514/322 |
| 5,962,535 A | * | 10/1999 | Miyamoto et al. | 514/724 |

FOREIGN PATENT DOCUMENTS

| JP | A7126017 | 5/1995 |
| JP | B2-2770571 | 4/1998 |
| JP | A11106353 | 4/1999 |

* cited by examiner

*Primary Examiner*—Zohreh Fay
*Assistant Examiner*—Brian-Yong Kwon
(74) *Attorney, Agent, or Firm*—Birch, Stewart, Kolasch & Birch, LLP

(57) ABSTRACT

The present invention provides a stable composition of an antidementia medicament. Specifically, it is a stabilized composition of an antidementia medicament comprising an antidementia medicament and an organic acid. As the organic acid, tosyllic acid, mesyllic acid, benzoic acid, salicylic acid, tartaric acid, citric acid and the like are particularly preferable.

10 Claims, No Drawings

STABILIZED COMPOSITION COMPRISING ANTIDEMENTIA MEDICAMENT

This application is the national phase under 35 U.S.C. §371 of PCT International Application No. PCT/JP99/01686 which has an International filing date of Mar. 31, 1999, which designated the United States of America.

FIELD OF INDUSTRIAL APPLICATION

The present invention relates to a stabilized composition of an antidementia medicament, especially, donepezil and also to a method of stabilizing donepezil.

PRIOR ART

Along with the emergence of a recent social problem concerning care of senile dementia, remedies for the senile dementia have been energetically developed. Among these, donepezil has an acetylcholine esterase inhibitory effect and is highly evaluated for its usefulness as a remedy for slight to medium degree of Alzheimer's dementia. Because donepezil is a basic medicament, it is provided as a salt of hydrochloric acid.

While, when medicaments are administered to patients, an appropriate dosage form is selected from tablets, capsule agents, powders, granules, ointments, injections, syrups and the like. In pharmaceutical preparations, various ideas are carried out corresponding to each dosage form. For example, percutaneous administration is known as one of the routes of administration to patients to whom chemicals can be orally administered with difficulty. In general, a medicament which is a salt has inferior penetrability into the skin; therefore medicaments are frequently made into a free form to formulate these drugs in percutaneous pharmaceuticals.

However, the stability of a medicament differs depending on the state of the medicament such as a salt state and a free state. The state of the medicament sometimes causes a hindrance to pharmaceutical preparations. There is the case where antidementia medicament, particularly, donepezil becomes unstable to light and/or heat when it is prepared and hence attention must be paid. In view of this situation, the inventors of the present invention have conducted intensive studies to increase the stability to light and/or heat and, as a result, found that the subject can be solved by the following means and completed the present invention.

DISCLOSURE OF THE INVENTION

The present invention is a stabilized composition of an antidementia medicament comprising an antidementia medicament and an organic acid. The present invention is a method of stabilizing an antidementia medicament by adding an organic acid to an antidementia medicament.

Specific examples of the antidementia medicament of the present invention include donepezil, TAK-147, CP118954 revastigmine, metrifonate, galanthamine and the like. Donepezil is generally used in the form of donepezil hydrochloride, as a therapeutic agent for Alzheimer's disease from slight to middle degrees. Chemical name thereof is 1-benzyl-4-(5,6-dimethoxyindanone-2-yl) methylpyperidine. Chemical names of TAK-147 and CP118954 are 3-[1-(phenylmethyl)pyperidine-4-yl]-1-(2,3,4,5-tetrahydro-1H-1-benzazepine-8-yl)-1-propane fumarate, and 5,7-dihydro-3-[2-[1-(phenylmethyl)-4-pyperidinyl]ethyl]-6H-pyrrolo[4,5-f]-1,2-benzisoxazole-6-one maleate, respectively. The structural formulae of these compounds are as follows.

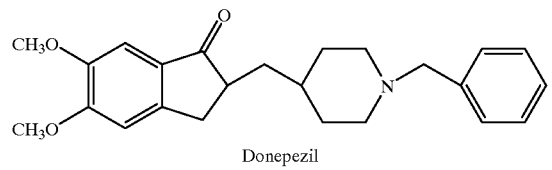
Donepezil

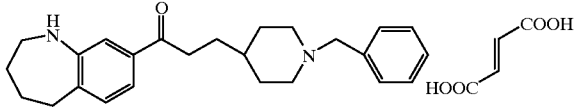
TAK-147

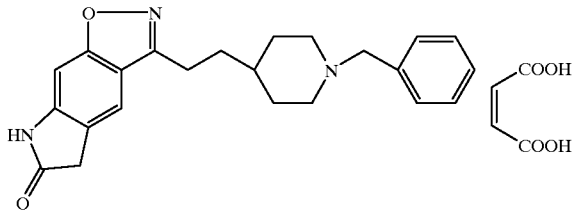
CP118954

No particular limitation is imposed on the organic acid used in the present invention. The examples thereof include higher fatty acid such as tosyllic acid, mesyllic acid, benzoic acid, salicylic acid, tartaric acid, citric acid, fumaric acid, maleic acid and stearic acid. Particularly, mesyllic acid, salicylic acid and citric acid are preferable. The organic acids may be used singly or by mixing two or more. Citric acid has a particularly excellent effect on the heat stability of donepezil.

The organic acid may be added in an amount of 0.1 to 10 parts by weight to 1 part by weight of the antidementia medicament. The amount of the organic acid is preferably 0.2 to 5 parts by weight and more preferably 0.2 to 2 parts by weight.

Although no particular limitation is imposed on the ratio of donepezil to the organic acid, the amount of the organic acid is usually 0.1 to 10 parts by weight, preferably 0.2 to 5 parts by weight and more preferably 0.2 to 2 parts by weight to 1 part by weight of donepezil.

The composition of the present invention may be used in a form such as tablets, granules, powders, ointments, injections or syrups. Each form is produced by a conventionally known method. For example, the granules can be produced as follows: the antidementia medicament is mixed with fillers such as lactose, mannitol, corn starch and crystal cellulose, a binder such as hydroxypropyl cellulose and polyvinylpyrrolidone dissolved in a solvent such as water is added thereto, mixed, kneaded and then granulated using an extrusion granulator. The ointments can be used together with the so-called ointment bases such as liquid paraffin, hydrogenated oil, vegetable oil, squalene, higher alcohols, higher fatty acid, esters of higher fatty acid, glycerol, water, antiseptics and dyes, and may be produced by a usually used method.

Syrups are prepared by dissolving the antidementia medicament together with sweetener such as sucrose, xylitol, mannitol and glucose in water. Further, a flavoring agent such as vanilla essence may be added if necessary.

According to the present invention, the stability of donepezil is significantly increased. The effects of the present invention will be shown by way of concrete examples.

STABILIZATION TEST EXAMPLES

An ethanol/water (1/1) solution containing 1 mg/ml of donepezil was prepared. Tosyllic acid, mesyllic acid, benzoic acid, salicylic acid, tartaric acid and citric acid are respectively added to the solution in amount by mol equivalent to donepezil. 5 ml of each resulting solution was sealed in a transparent glass ample. The pH of each resulting solution was 5.74, 5.84, 5.73, 5.89, 5.75 and 3.28. The pH of the solution in the case of adding no organic acid was 5.63. Each glass ample was stored at room temperature under 1000 Lux for one month to measure the content. While each same solution was separately stored at a cold place for a month and the content was measured to determine the residual ratio under illumination of light. The content was measured by using high performance liquid chromatography. The results are shown in Table 1.

TABLE 1

| Organic acid | Storage condition | Outward appearance | Peak hight | Residual ratio (%) |
|---|---|---|---|---|
| not added | cold place | – | 41367 | 100.0 |
|  | 121° C., 20 min | – | 42946 | 103.8 |
|  | 1000 Lux, 1 month | ++ | 35139 | 84.9 |
| tosyllic acid | cold place | – | 42967 | 100.0 |
|  | 121° C., 20 min | – | 44320 | 103.2 |
|  | 1000 Lux, 1 month | + | 41856 | 97.4 |
| mesyllic acid | cold place | – | 43386 | 100.0 |
|  | 121° C., 20 min | ± | 44202 | 101.9 |
|  | 1000 Lux, 1 month | – | 43164 | 99.5 |
| benzoic acid | cold place | – | 42667 | 100.0 |
|  | 121° C., 20 min | – | 43547 | 102.1 |
|  | 1000 Lux, 1 month | ++ | 38813 | 91.0 |
| salicylic acid | cold place | – | 43075 | 100.0 |
|  | 121° C., 20 min | – | 43814 | 101.7 |
|  | 1000 Lux, 1 month | + | 43326 | 100.6 |
| tartaric acid | cold place | – | 44598 | 100.0 |
|  | 121° C., 20 min | – | 43284 | 97.1 |
|  | 1000 Lux, 1 month | – | 42926 | 96.3 |
| citric acid | cold place | – | 42583 | 100.0 |
|  | 121° C., 20 min | – | 43102 | 101.2 |
|  | 1000 Lux, 1 month | – | 42346 | 99.4 |

As shown in Table 1, the composition according to the present invention was improved in light stability more significantly than the samples to which nothing was added. The compositions containing each of, particularly, mesyllic acid, salicylic acid and citric acid were considered to be not almost decomposed since no peak of the decomposed materials was observed on a chromatogram.

Because percutaneous pharmaceuticals such as ointments are frequently exposed to light after they are applied to the skin, the composition according to the present invention is particularly useful.

Next, each of citric acid and maleic acid and as a control, hydrochloric acid and phosphoric acid was added to a 5 mg/5 ml donepezil solution in an amount shown in Table 2 and each resulting solution was stored at 60° C. for one month to measure the content. The pH was adjusted to 3.75. The results are shown in Table 2.

TABLE 2

| Organic acid |  | The ratio of the area of impurities on a chromatogram (%) |
|---|---|---|
| Citric acid | 0.22 mg | 0.07 |
|  | 15 mg | 0.09 |
|  | 30 mg | 0.10 |
|  | 45 mg | 0.10 |
| malic acid | 15 mg | 0.10 |
| Control |  |  |
| hydrochloric acid | 5 mg | 0.42 |
| phosphoric acid | 15 mg | 0.43 |

Further, each of citric acid and as a control, hydrochloric acid was added to a 5 mg/5 ml donepezil solution containing 10% of polyvinylpyrrolidone (PVP) in an amount shown in Table 3 and each resulting solution was stored at 60° C. for one month to measure the content. The results are shown in Table 3.

TABLE 3

| Organic acid |  | The ratio of the area of impurities on a chromatogram (%) |
|---|---|---|
| Citric acid | 15 mg | 1.34 |
|  | 45 mg | 1.26 |
| Control |  |  |
| hydrochloric acid | 5 mg | 2.45 |

It is clear from Tables 2 and 3 that the composition of the present invention is reduced in the ratio of the area of impurities on a chromatogram of high performance liquid chromatography more significantly than the control sample and is increased in stability also to heat.

EXAMPLES

The present invention will be hereinafter described in more detail by referring to Examples, however the present invention is not limited by them.

Example 1

5 g of donepezil, 5 g of tosyllic acid, 150 g of lactose, 200 g of mannitol and 20 g of low-substituted hydroxypropyl cellulose were mixed. To the mixture was gradually added 7 g of hydroxypropyl cellulose dissolved in 50 ml of water, which was then mixed and kneaded. The kneaded mixture was charged into an extrusion granulator to produce a granule. The screen was designed to be 0.4 mm.

Example 2

500 mg of donepezil, 200 mg of citric acid and 2000 mg of glucose were dissolved in water for injection. The pH of the solution was adjusted to 5.5 by adding 0.1N sodium hydroxide. Then, water for injection was further added to the solution such that the volume was 100 ml. Each 1 ml of the resulting solution was pipetted into an ample. The ample was melt-closed and then sterilized at 121° C. for 15 minutes to produce an injection.

Example 3

100 mg of donepezil, 300 mg of sodium saccharate and 50 mg of citric acid were dissolved in 50 ml purified water. The pH of the solution was adjusted to 5.5 by adding 0.1N sodium hydroxide. Then, 300 mg of methyl parabene and 20 mg of propyl parabene which were dissolved in a small amount of propylene glycol were added thereto. Purified water was further added such that the total volume of the resulting solution was 100 ml to produce a syrup.

What is claimed is:

1. An antidementia medicament composition, comprising:
   an antidementia medicament and
   an organic acid,
wherein the antidementia medicament is donepezil and the organic acid is selected from the group consisting of tosyllic acid, mesyllic acid, benzoic acid, salicylic acid, tartaric acid, citric acid and combinations thereof, wherein the organic acid is not added to form a salt.

2. The composition as claimed in claim 1, which is stabilized to light and/or heat.

3. A method for stabilizing an antidementia medicament, which comprises the step of:

adding an organic acid to an antidementia medicament, wherein the antidementia medicament is donepezil and the organic acid is selected from the group consisting of tosyllic acid, mesyllic acid, benzoic acid, salicylic acid, tartaric acid, citric acid and combinations thereof, wherein the organic acid is not added to form a salt.

4. The method as claimed in claim 3, which comprises the step of stabilizing to light and/or heat.

5. The method as claimed in claim 3, wherein the organic acid is added in an amount of 0.1 to 10 parts by weight to 1 part of the antidementia medicament.

6. The antidementia medicament composition according to claim 1, wherein the amount of organic acid is 0.1 to 10 parts by weight to 1 part by weight of donepezil.

7. The antidementia medicament composition according to claim 1, wherein the amount of organic acid is 0.2 to 5 parts by weight to 1 part by weight of donepezil.

8. The antidementia medicament composition according to claim 1, wherein the amount of organic acid is 0.2 to 2 parts by weight to 1 part by weight of donepezil.

9. The method for stabilizing an antidementia medicament according to claim 3, wherein the amount added of organic acid is 0.2 to 5 parts by weight to 1 part by weight of donepezil.

10. The method for stabilizing an antidementia medicament according to claim 3, wherein the amount added of organic acid is 0.2 to 2 parts by weight to 1 part by weight of donepezil.

* * * * *